United States Patent [19]

Butler et al.

[11] 4,389,881
[45] Jun. 28, 1983

[54] METHOD OF MEASURING AN AIR TO FUEL RATIO

[75] Inventors: James W. Butler, Dearborn Heights; Alex D. Colvin, Oak Park, both of Mich.

[73] Assignee: Ford Motor Company, Dearborn, Mich.

[21] Appl. No.: 288,874

[22] Filed: Jul. 31, 1981

[51] Int. Cl.³ .......................................... G01M 15/00
[52] U.S. Cl. ....................................... 73/116; 73/1 G; 436/160
[58] Field of Search ...................... 73/1 G, 116, 27 R; 123/440; 436/155, 160

[56] References Cited

U.S. PATENT DOCUMENTS 4,263,652 4/1981 Henrich ................................ 73/1 G
4,348,732 9/1982 Kreft .................................... 73/1 G Primary Examiner—Jerry W. Myracle
Attorney, Agent, or Firm—William E. Johnson; Olin B. Johnson

[57] ABSTRACT

A method is disclosed for measuring the air to fuel ratio of an air/fuel mixture being supplied to a combustion process. This method has the following steps. An oxygen sensor station is established at which the sensor senses the difference in oxygen partial pressure from a first reference side thereof to a second oxygen measurement side thereof. The oxygen sensor is maintained at a predetermined temperature and at a pressure below atmospheric pressure. The oxygen sensor is calibrated so that the measurement thereby of an EMF between the first reference side thereof and the second oxygen measurement side thereof is indicative of the oxygen partial pressure in a gas stream passing by the oxygen measurement side thereof. A sample gas stream is drawn into the pressure across the second oxygen measurement side of the oxygen sensor. This pressure is one which allows samples to be drawn at a constant flow rate independent of that pressure. A fixed amount of oxygen is added to the sample gas stream. The oxygen in the sample gas stream is reacted with oxidizable species contained in the sample gas stream prior to passing the sample gas stream across the second oxygen measurement side of the oxygen sensor. The pressure of the gas sample is measured. The air to fuel ratio of the air/fuel mixture is determined from the measured EMF of the oxygen sensor, the total pressure of the sample gas stream and the known oxygen addition rate. Suitable oxygen sensors may be formed zirconia or titania.

7 Claims, 1 Drawing Figure

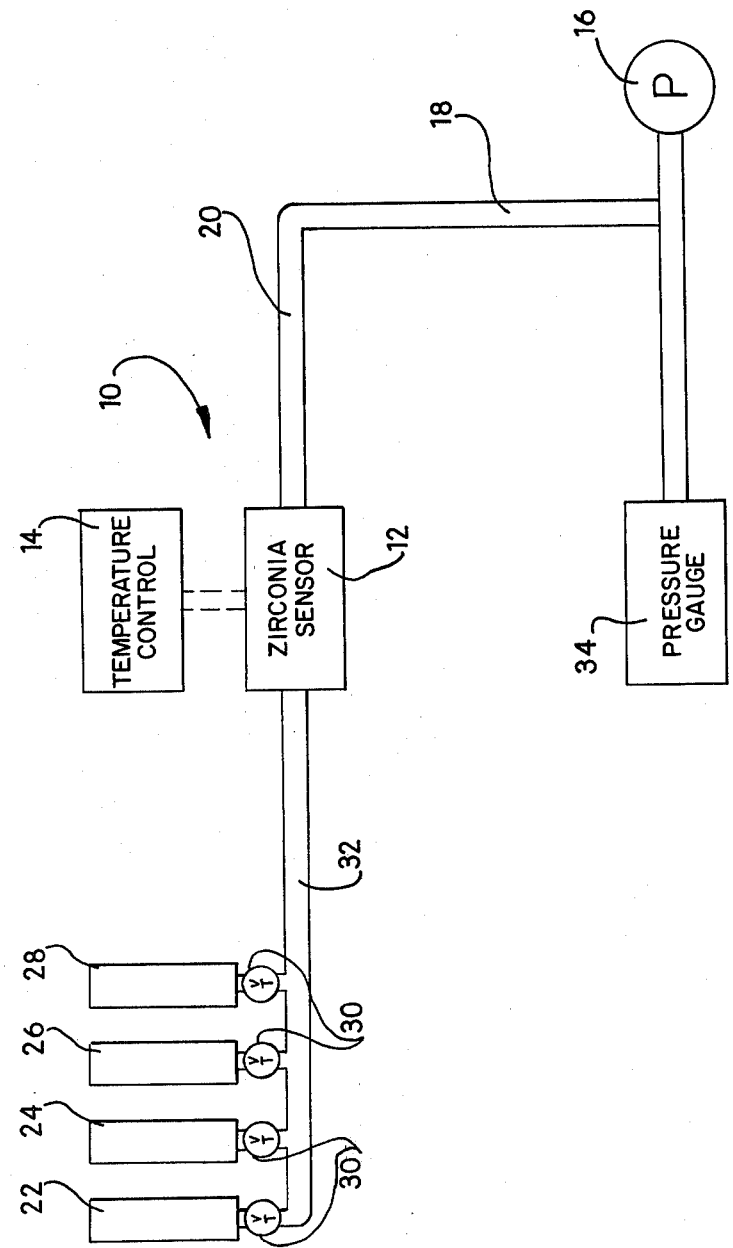

METHOD OF MEASURING AN AIR TO FUEL RATIO

BACKGROUND OF THE INVENTION AND PRIOR ART STATEMENT

No prior art search was conducted on the subject matter of this specification in the U.S. Patent and Trademark Office or in any other search facility. We are unaware of any prior art more relevant to the subject matter of this disclosure than that which is set forth below. U.S. Ser. No. 265,316, filed May 20, 1981, entitled "Methods of Monitoring a Combustion System", is assigned to Ford Motor Company, the assignee of the present application. The 265,316 application set forth methods of monitoring a combustion system which were developed before the method set forth in this specification. Included among the many methods set forth in the aforementioned application is a method of measuring the air to fuel ratio of an air/fuel mixture being supplied to a combustion process. The entire Ser. No. 265,316 application is hereby incorporated by reference.

The method of obtaining the air/fuel ratio of an air/fuel mixture being supplied to a combustion process as taught in the aforementioned Ser. No. 265,316 specification is fairly complex because it is a versatile instrument capable of other combustion related measurements. The present specification teaches a method which is less sophisticated than the method taught in the prior application. The method taught in the present specification does, however, give one an excellent indication of the air to fuel ratio of an air/fuel mixture being supplied to a combustion process. However, the method taught in the present specification is not capable of measuring other engine parameters taught in the previous method.

The more complex method of measuring the air to fuel ratio of air/fuel mixture being supplied to a combustion process as taught in the prior specification Ser. No. 265,316 is generally carried as follows. An air/fuel mixture is continuously passed through a combustion process to generate a first stream of gaseous material. This first stream of gaseous material may contain (a) unburned fuel, (b) partially oxidized fuel, (c) carbon monoxide, (d) carbon dioxide, (e) water vapor, (f) nitrogen, (g) oxygen, (h) inert gases normally found in air, or (i) a mixture of any or all of (a) through (h). A sample portion of the first stream of gaseous material is continuously withdrawn into a volume at a first pressure below atmospheric pressure. The first pressure below atmospheric pressure is a pressure that at the temperature of the sample portion continuously withdrawn the water vapor contained therein will not condense. The sample portion continuously withdrawn forms a second stream of gaseous material that has the same compositional makeup on a volume percentage basis as the first stream of gaseous material but at a reduced pressure.

A controlled source of oxygen addition is continuously provided to the second stream of gaseous material. The controlled source of oxygen addition is continuously controlled by application of a control signal thereto. The control signal is applied in a manner that the oxygen is added to the second stream of gaseous material at a rate proportinal to the strength of the control signal applied to the controlled source of oxygen addition. The control signal is continuously developed to a strength which results in the controlled source of oxygen addition adding to the second stream of gaseous material sufficient oxygen that there is after oxygen addition a predetermined amount of oxygen in excess of that required to stoichiometrically oxide any (a) unburned fuel, (b) partially oxidized fuel, and (c) carbon monoxide to (d) carbon dioxide and (e) water vapor.

A sample portion of the second stream of gaseous material is continuously withdrawn into a volume at a second pressure substantially below the first pressure. The sample is withdrawn after the oxygen has reacted with (a) unburned fuel, (b) partially oxidized fuel, and (c) carbon monoxide. This second pressure is a pressure that, at the temperature of the sample portion continuously withdrawn from the second stream of gaseous material, the water vapor contained therein will not condense. The sample portion continuously withdrawn forms a third stream of gaseous material that has the same composition makeup based on fully oxidized carbon and hydrogen on a molar basis as the second stream of gaseous material plus added oxygen but at a reduced pressure.

The third stream of gaseous material is continuously subjected to analysis by a mass spectrometer to generate on a continuous basis an output signal. The output signal developed is indicative of the ratio of oxygen to nitrogen in the third stream of gaseous material. The control signal for application to the controlled source of oxygen is continuously generated from the output signal generated by the mass spectrometer. The control signal strength is generated in a manner that: (1) when the oxygen signal of the third stream of gaseous material being measured by the mass spectrometer is at a predetermined level, the control signal strength has a predetermined strength which ensures the predetermined amount of oxygen in excess of that required to stoichiometrically oxidize the components is added to the second stream of gaseous material; and (2) when the oxygen signal of the third stream of gaseous material being measured by the mass spectrometer falls away from the predetermined level, the control signal has a strength that ensures an amount of oxygen greater than the predetermined amount of oxygen is added to the second stream of gaseous material.

In this manner, the measured oxygen signal is returned to the predetermined level, the instantaneous amount of oxygen being added to the second stream of gaseous material being a direct measure of the air to fuel ratio of the air/fuel mixture being burned in the combustion process.

As is readily apparent, the methodology of the Ser. No. 265,316 specification is rather sophisticated, the sophistication giving rise to an extremely accurate measurement by the method steps of the air to fuel ratio of the air/fuel mixture being burned in the combustion process.

It is a principal object of this invention to provide a method of measuring the air to fuel ratio of an air/fuel mixture being supplied to a combustion process which is relatively simple to carry out, but yet which provides an accurate measurement of the desired parameter.

It is another object of this invention to provide a method of measuring the air to fuel ratio of an air/fuel mixture which can be carried out by instrumentated apparatus of relatively simple design and construction.

SUMMARY OF THE INVENTION

This invention relates to a method of measuring the air to fuel ratio of a mixture and, more particularly, to a method of measuring the air to fuel ratio of an air/fuel mixture being supplied to a combustion process.

In accordance with the general teachings of the method of this invention, the air to fuel ratio of an air/fuel mixture being supplied to a combustion process is measured in the following manner. An oxygen sensor station is established at which the sensor senses the ratio of oxygen partial pressure from a first reference side thereof to a second oxygen measurement side thereof. The oxygen sensor is maintained at a predetermined temperature and at a predetermined pressure below atmospheric pressure. The oxygen sensor is calibrated so that the measurement thereby of an EMF between the first reference side therof and the second oxygen measurement side thereof is indicative of the oxygen partial pressure in a gas stream passing by the oxygen measurement side thereof. A sample gas stream is drawn at the predetermined reduced pressure across the second oxygen measuring side of the oxygen sensor. The predetermined pressure is one which allows the sample gas stream to be drawn at a constant flow rate independent of that predetermined pressure. A fixed amount of oxygen is added to the sample gas stream. Oxygen contained in the sample gas stream is allowed to react with oxidizable species contained in the sample gas stream prior to passing the sample gas stream across the second oxygen measuring side of the oxygen sensor. The total pressure of the sample gas stream is measured. The air to fuel ratio of the air/fuel mixture is determined through the interrelationship of the EMF measured by the oxygen sensor, the total pressure of the sample gas stream, and the known oxygen addition rate.

The oxygen sensor station may be defined, for example, by a zirconia oxygen sensor, or for example, by a titania oxygen sensor, both of which are well known to skilled artisans.

The method of this specification is relatively easy to carry out and does not require the sophisticated hardware required by the method set forth in U.S. patent specification Ser. No. 265,316.

BRIEF DESCRIPTION OF THE DRAWINGS

The novel features that are considered characteristic of the invention are set forth with particularity in the appended claims. The invention itself, however, both as to its organization and its method of operation, together with additional objects and advantages thereof, will best be understood from the following description of specific embodiments when read in connection with the accompany drawing in which the FIGURE shows a schematic presentation of hardware required to carry out the method of this invention.

DESCRIPTION OF THE PREFERRED EMBODIMENT

The following description is what we consider to be a preferred embodiment of our method of measuring the air to fuel ratio of an air/fuel mixture being supplied to a combustion process. The following description also sets forth what we now contemplate to be the best mode of carrying out our method. This description is not intended to be a limitation upon the broader principles of this method and, while preferred materials are used to illustrate the method in accordance with the requirements of the patent laws, it does not mean that the method is operative only with the stated materials, as other materials may be substituted therefor.

Also, for example, the method disclosed herein may be successfully used with materials yet to be developed by skilled atisans, such as new electrolyte materials which are capable of measuring oxygen partial pressures. It is therefore contemplated by us that the method disclosed may also be successfully used with materials which are yet to be developed because of principles of operation of the method remain the same, regardless of the particular materials subjected to the method or used with the method.

In the FIGURE there is schematically illustrated apparatus, generally designated by the numeral 10, for carrying out a preferred embodiment of the method of this invention. The principal element of the apparatus is a zirconia oxygen sensor station 12 and a temperature control device 14, the relationship and function of which are fully described in our copending application U.S. Ser. No. 273,517, which application is hereby incorporated by reference. As set forth in that specification, a zirconia sensor, or other oxygen sensor, has an electrolyte which defines two sides of the sensor. A first side of the sensor is an oxygen reference side and the second side is an oxygen measurement side. In general application, an oxygen reference material such as pure oxygen or ambient air is blown or moved over the first oxygen reference side of the zirconia oxygen sensor to define a known condition. An unknown, having an unknown oxygen content, is flowed over the second oxygen measurement side of the zirconia sensor. If there is a difference in oxygen partial pressure on the two sides of the zirconia sensor's electrolyte, an EMF will appear through the electrolyte, the EMF being a measurement of the difference in oxygen partial pressure and thus being a positive indication of the partial pressure of oxygen on the oxygen measurement side of the zirconia sensor.

As is also well known in the art, the zirconia oxygen sensor is fairly temperature dependent in that the EMF generated by a predetermined difference in oxygen partial pressures from the two sides of the electrolyte thereof is also a function of temperature. Thus, the EMF is generally measured at a predetermined temperature so that this variation of EMF with temperature is eliminated from the measurement variables thereby permitting an easy computation of the partial pressure of oxygen being measured on the oxygen measurement side of the zirconia oxygen sensor. Our copending U.S. application is directed to a method of ensuring an accurate temperature control for the operation of a zirconia sensor. For further details of this method, one is referred to the aforementioned specification.

Therefore, in accordance with the preferred embodiment of a method of measuring the air to fuel ratio of an air/fuel mixture being supplied to a combustion process, the following steps are carried out. An oxygen sensor station 12, such as the zirconia oxygen sensor, is established at which the sensor can sense the ratio of oxygen partial pressure from a first reference side thereof to a second measurement side thereof. The oxygen sensor is maintained at a predetermined temperature. The oxygen sensor station 12 is also maintained at a pressure below atmospheric pressure. This pressure is maintained by means of vacuum pump 16 working through vacuum lines 18 and 20. By a pressure below atmospheric pressure, we mean a pressure which is sufficient to allow any water vapor formed by the combustion process to remain in the gaseous phase. We prefer the predetermined pressure to be in a range from 0.01 to 0.2 atmospheres, and prefer that in most cases the method be carried out at a pressure of 0.05 atmospheres.

The next step of the method is a calibration step which will be explained in detail hereinbelow. However, before this explanation, suffice it to say that this calibration step is carried out at the initiation of the method of this invention. Once the calibration step has been carried out and the instrument properly calibrated, then the other steps in the method may be carried out. One may desire to go back occasionally during the run of the instrument to check the calibration thereof. However, it should be kept in mind that most measurement methods do require a calibrating step and that the step is carried out only at the initiation of the method and does not form a generally continuous part thereof. So, also in this case, the calibration step is one which is carried out at the initiation of the method and also from time to time during the method for recheck. It is intended in the appended claims that the calibrating step be understood as one which is carried out at the initiation of the method and maybe here and there during the method, but not a step that is continuously ongoing throughout the entire performance of the method.

Before we go any further in the discussion of this method, we wish to point out a special relationship between the pressure established at the oxygen sensor station 12 and the positions from which certain gases flow into the system in order to pass through the oxygen sensor station. In accordance with the teachings of the preferred method of this invention, there are four positions from which gases are drawn over the zirconia oxide sensor 12. These four positions are a zero gas station 22, a sample gas station 24, a first added air station 26, and a second added air station 28. Each of these stations are connected by means of a throttle valve 30—30 to a vacuum line 32 which is connected to the zirconia oxygen sensor station 12. A pressure is established in the vacuum line 32 and zirconia oxygen sensor station 12 which allows samples to be drawn at a constant flow rate through the throttle valves 30—30 independent of the pressure which has been established in the vacuum line and zirconia oxygen sensor station. Since the vacuum pump is a constant volume device (at these pressures), the constituent partial pressures, when additions are made, are additive instead of averaging each other, as is the case with other sampling systems.

In order to calibrate the zirconia oxygen sensor station 12, all of the throttle valves 30—30 are turned off except the one leading to the zero gas station 22. This zero gas station contains nitrogen gas. The nitrogen gas is drawn over through the oxygen sensor station 12 and a reading is taken of the output of the zirconia oxide electrolyte in millivolts.

Thereafter, the throttle valve 30 to the first added air station 26 is turned on. The first added air station contains a known quantity of oxygen in the gas sample. For example, the sample may be ambient air. A reading is also taken of this output for this sample from the zirconia oxygen sensor. The throttle to the second added air station 28 is now turned on. An EMF output is obtained at this time. A linear graph may then be established based upon a plot of the antilog of the millivolt reading from the zirconia oxygen sensor for each sample above described and the partial pressure of oxygen. One of the points used to establish this graph is the arithmetic sum of the points obtained from the data on the first added air station 26 and the second added air station 28. The data point used or established by the first zero gas station alone is used to establish a baseline for the air/fuel measurement.

Once the plot is obtained, it can be zeroed in the electrical equipment associated with the oxygen sensor station 12 in a known manner. By zeroing in, we mean that a zero indication on the millivolt reading from the oxygen sensor station is indicative of an exhaust gas operating under stoichiometric conditions, that is, the exhaust gases will contain no oxygen. If the output reading drops below zero, there is a positive indication that the exhaust gases are deficient in oxygen and reducing in nature. This would be produced in the situation where the air/fuel mixture burned in the internal combustion engine was rich of stoichiometric conditions, that is, fuel rich. If the signal is positive, this indicates lean air/fuel mixtures are being burned, that is, fuel deficient, and that excess oxygen is available in the system.

Once the zeroing in and calibrating has taken place, a sample gas is drawn from the sample gas station 24 and a fixed amount of oxygen is added from the one air station, 26. The addition of added air from the station 26 gives a fixed known addition to the measurement system of oxygen. The added air is allowed to react with oxidizable species contained in the sample gas stream.

A pressure gauge 34 is used to measure the pressure established by the vacuum pump 16, the oxygen sensor station 12, and the vacuum line 32.

The air to fuel ratio of the air/fuel mixture being burned in the combustion process is determined from the EMF measured by the zirconia oxygen sensor station, the pressure of the oxygen sensor station 12 and vacuum line 32, and the known oxygen addition rate. One is able to determine the air/fuel ratio since the air/fuel ratio is directly related to the fraction of oxygen measured in the combustion process exhaust gas.

The thing that makes the method of this invention so very unique is the fact that the pressure across the oxygen sensor station 12 is a pressure which allows samples to be drawn at a constant flow rate from a sample source, that constant flow rate being independent of the pressure established at the sensor station. This is true of the flow rate through the throttling valve for each of the sample stations 22 through 28. However, we compare it to a sonic flow because it is a flow which is independent of downstream pressure and thus, as one or more streams are allowed to pass into the vacuum line 32, there is no change in the rate of flow of one or the other of the streams. Each of the streams will be sampled at a constant flow rate, regardless of whether one or more of the gas streams are on. In other sampling systems where this unique arrangement is not carried out, and the downstream pressure is relatively high, a change by adding another gas stream normally changes the amount of a previous gas stream flowing into the sampling line. However, in our situation there is no change, as one or more of the sampling lines are opened or closed.

While particular embodiments of the invention have been illustrated and described, it will be obvious to those skilled in the art that various changes and modifications may be made without departing from the invention, and it is intended to cover in the appended claims all such modifications and equivalents as fall within the true spirit and scope of this invention.

What is claimed is:

1. A method of measuring the air to fuel ratio of an air/fuel mixture being supplied to a combustion process which comprises the steps of:

establishing an oxygen sensor station at which said sensor senses the difference in oxygen partial pressure from a first reference side thereof to a second oxygen measurement side thereof;

maintaining said oxygen sensor at a predetermined temperature and a predetermined pressure below atmospheric pressure;

calibrating said oxygen sensor so that the measurement thereby of an EMF between said first reference side thereof and said second oxygen measurement side thereof is indicative of the oxygen partial pressure in a gas stream passing by said oxygen measurement side thereof;

drawing at said predetermined pressure, a sample gas stream across said oxygen measurement side of said oxygen sensor, said predetermined pressure being one which allows said sample gas stream to be drawn at a constant flow rate independent of that predetermined pressure;

adding a fixed amount of oxygen to said sample gas stream;

reacting said oxygen in said sample gas stream with oxidizable species contained in said sample gas stream prior to passing said sample gas stream across said second oxygen measuring side of said oxygen sensor;

measuring said predetermined pressure; and determining the air to fuel ratio of the air/fuel mixture from the EMF measured by said oxygen sensor, the predetermined pressure of said sample gas stream and the known oxygen addition rate.

2. The method of claim 1, in which said oxygen sensor station contains a zirconia oxygen sensor.

3. The method of claim 1, in which said oxygen sensor station contains a titania oxygen sensor.

4. The method of claim 1 or 2, in which said predetermined pressure is in the range from 0.01 to 0.2 atmospheres.

5. The method of claim 1 or 3, in which said predetermined pressure is in the range from 0.01 to 0.2 atmospheres.

6. The method of claim 1 or 2, in which said predetermined pressure is 0.05 atmospheres.

7. The method of claim 1 or 3, in which said predetermined pressure is 0.05 atmospheres.

* * * * *